United States Patent
Bashiri et al.

(10) Patent No.: US 10,751,208 B2
(45) Date of Patent: *Aug. 25, 2020

(54) MEDICAL IMPLANT DELIVERY SYSTEM AND METHOD OF USE

(71) Applicants: STRYKER CORPORATION, Kalamazoo, MI (US); STRYKER EUROPEAN HOLDINGS I, LLC, Kalamazoo, MI (US)

(72) Inventors: Mehran Bashiri, San Carlos, CA (US); Elena Oo, Fremont, CA (US); Henry Luk, San Francisco, CA (US)

(73) Assignees: STRYKER EUROPEAN HOLDINGS I, LLC, Kalamazoo, MI (US); STRYKER CORPORATION, Kalamazoo, MI (US)

( * ) Notice: Subject to any disclaimer, the term of this patent is extended or adjusted under 35 U.S.C. 154(b) by 153 days.

This patent is subject to a terminal disclaimer.

(21) Appl. No.: 16/152,334

(22) Filed: Oct. 4, 2018

(65) Prior Publication Data

US 2020/0107948 A1  Apr. 9, 2020

(51) Int. Cl.
*A61F 2/966* (2013.01)
*A61F 2/958* (2013.01)
(Continued)

(52) U.S. Cl.
CPC .............. *A61F 2/966* (2013.01); *A61F 2/958* (2013.01); *A61F 2002/9665* (2013.01);
(Continued)

(58) Field of Classification Search
CPC .. A61F 2/95; A61F 2/958; A61F 2/962; A61F 2/966; A61F 2002/9505;
(Continued)

(56) References Cited

U.S. PATENT DOCUMENTS

| 4,733,665 | A | * | 3/1988 | Palmaz | A61F 2/915 |
| | | | | | 606/108 |
| 8,337,543 | B2 | * | 12/2012 | Jordan | A61F 2/95 |
| | | | | | 623/1.12 |

(Continued)

FOREIGN PATENT DOCUMENTS

EP         2532324      12/2012

OTHER PUBLICATIONS

PCT International Search Report and Written Opinion for International Appln. No. PCT/US2019/053138, Applicant Stryker Corporation, dated Feb. 21, 2020 (14 pages).

*Primary Examiner* — Melanie R Tyson
(74) *Attorney, Agent, or Firm* — Vista IP Law Group, LLP (57) ABSTRACT

An implant delivery system includes a delivery catheter and a delivery mechanism slidably disposed in a lumen of the delivery catheter. The delivery mechanism includes an annular channel and a compressible annular bushing disposed within the annular channel. The annular bushing is configured for being placed between a compressive profile and an expanded profile. The implant delivery system further includes an implant coaxially disposed between the delivery catheter and the delivery mechanism. The delivery catheter lumen is sized to maintain an engagement element of the implant within the annular channel and to urge the annular bushing into the compressive profile. The implant constrains a distal tip of the delivery mechanism to assume a straight geometry. The distal tip is configured for assuming a curved geometry when the implant is deployed from the delivery catheter.

18 Claims, 10 Drawing Sheets

(51) Int. Cl.
  *A61M 25/01*  (2006.01)
  *A61M 25/00*  (2006.01)

(52) U.S. Cl.
  CPC ..... *A61M 25/0041* (2013.01); *A61M 25/0068* (2013.01); *A61M 25/0108* (2013.01); *A61M 2025/0081* (2013.01)

(58) Field of Classification Search
  CPC ...... A61F 2002/9511; A61F 2002/9522; A61F 2002/9534; A61F 2002/9583; A61F 2002/9665
  See application file for complete search history.

(56) References Cited

U.S. PATENT DOCUMENTS

| | | | |
|---|---|---|---|
| 2010/0191221 A1* | 7/2010 | Eidenschink | A61F 2/856 604/509 |
| 2013/0261730 A1 | 10/2013 | Bose et al. | |
| 2014/0088678 A1 | 3/2014 | Wainwright et al. | |
| 2014/0180387 A1 | 6/2014 | Khenansho et al. | |
| 2014/0180397 A1 | 6/2014 | Gerberding et al. | |

* cited by examiner

MEDICAL IMPLANT DELIVERY SYSTEM AND METHOD OF USE

FIELD

The present disclosure relates generally to medical devices and intravascular medical procedures and, more particularly, to devices and methods for delivering an implant to a target site in a blood or other body vessel.

BACKGROUND

The use of intravascular medical devices has become an effective method for treating many types of vascular disease. In general, a suitable intravascular device is inserted into the vascular system of the patient and navigated through the vasculature to a desired target site. Using this method, virtually any target site in the patient's vascular system may be accessed, including the coronary, cerebral, and peripheral vasculature.

Figure 1:
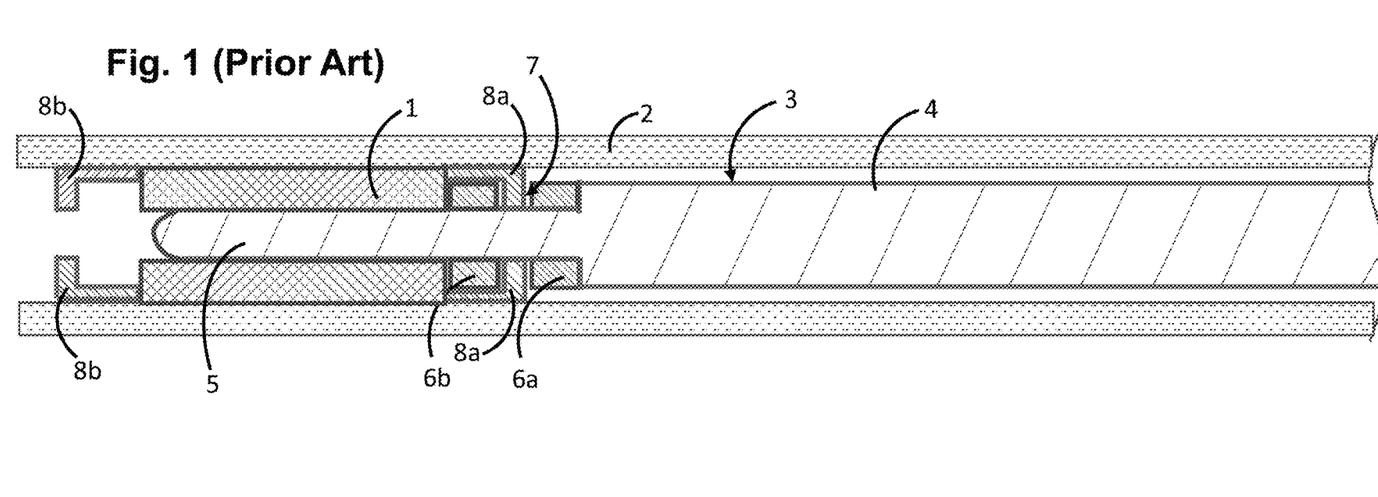
FIG. 1 is a cross-sectional view of a prior art implant delivery system.

Medical implants, such as stents, stent grafts, flow-diverters, and vena cava filters, are often utilized in combination with a delivery device for placement at a desired location within the body. For example, with reference to FIG. 1, a medical implant 1, such as a stent, may be loaded into a delivery sheath 2 via a stent delivery mechanism 3. The stent delivery mechanism 3 comprises a delivery wire 4 having a distal tip 5 on which the stent 1 is affixed. The stent delivery mechanism 3 further comprises a proximal bumper 6a and a distal bumper 6b between which there is formed an annular channel 7 for engaging the stent 1 in a manner that allows the stent 1 to be axially displaced within the delivery sheath 2, while releasing the stent 1 once it is deployed outside of, and therefore no longer contained by, the delivery sheath 2. In this embodiment, the stent 1 includes one or more proximal radiopaque marker 8a (two shown) and one or more distal radiopaque markers 8b (two shown). The proximal radiopaque markers 8a reside within the annular channel 7 between the bumpers 6a, 6b to facilitate engagement between the stent 1 and the stent delivery mechanism 3.

Figure 2A:
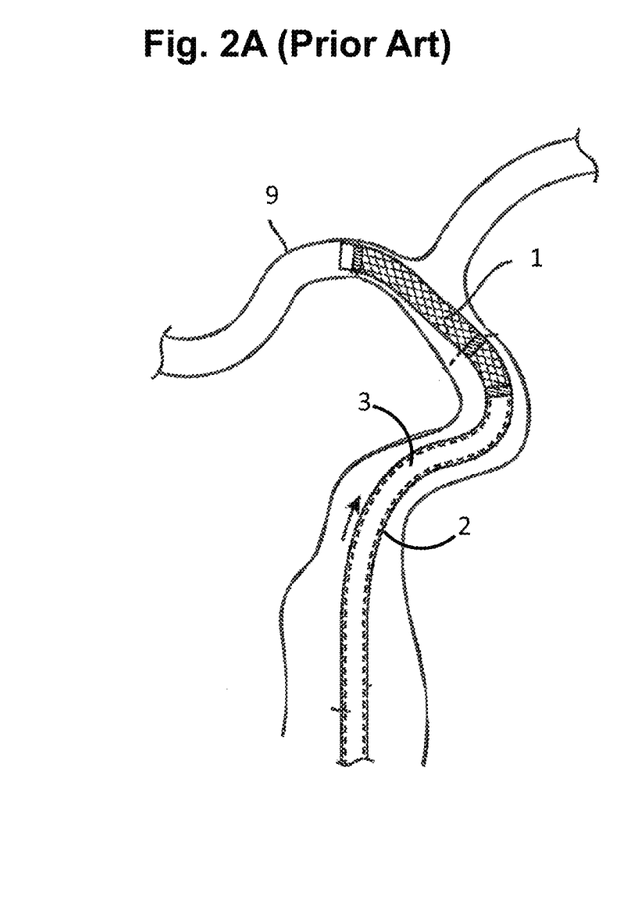
FIGS. 2A-2D are plan views illustrating a prior art method using the implant delivery system of FIG. 1 to deploy a stent within the vasculature of a patient.
Figure 2B:
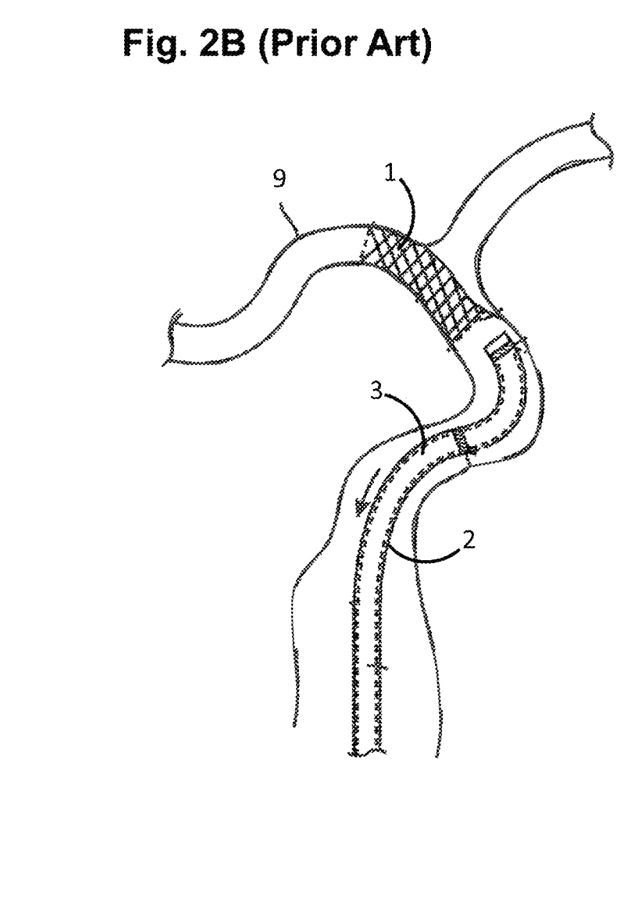

The delivery sheath 2, with the stent 1 in its reduced undeployed configuration, may be introduced into the lumen of a blood vessel 9, and delivered to a target location within the blood vessel 9, as illustrated in FIG. 2A. Once delivered to a target location within the body, the stent 1 may then be deployed out of the delivery sheath 2 via the stent delivery mechanism 3 by retracting the delivery sheath 2 in the proximal direction, and expanded to an enlarged configuration within the blood vessel 9 to support and reinforce the wall of the vessel 9, while maintaining the vessel 9 in an open, unobstructed condition, as illustrated in FIG. 2B. The stent 1 may be configured for being self-expanding, expanded by a stored potential radial force such as a balloon, or a combination of self-expanding and balloon-expanded.

Oftentimes, it is desirable to remove the delivery sheath 2 from the patient while the stent delivery mechanism 3 remains in the patient, re-cross the deployed stent 1 with the stent delivery mechanism 3, and guide another device (not shown) over the stent delivery mechanism 3 into engagement with the deployed stent 1. For example, the other device may be a balloon catheter that is expanded within the deployed stent 1 to either expand the stent 1 into contact with the wall of the vessel 9 if the stent is not self-expanding, or if the stent is self-expanding, to ensure that the stent is an opposing engagement with the wall of the vessel 9.

Figure 2C:
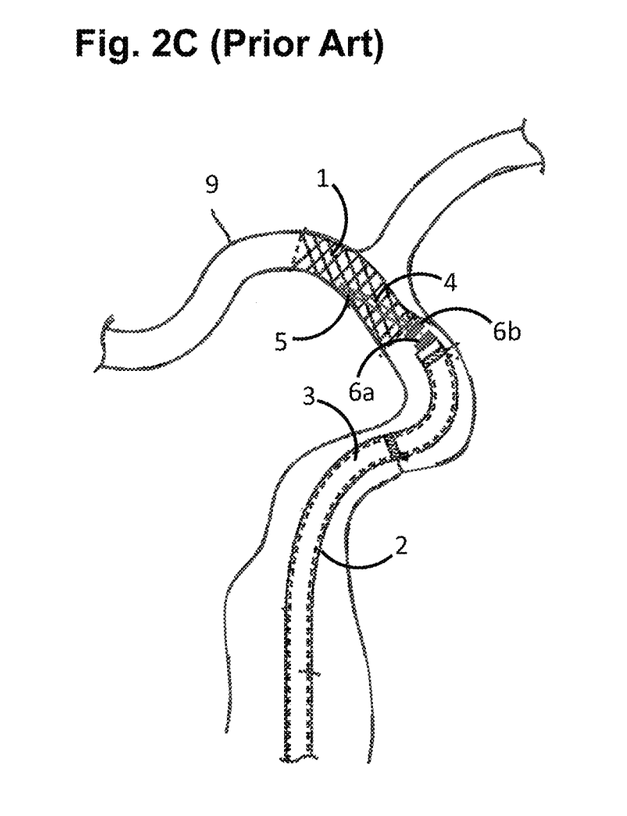
Figure 2D:
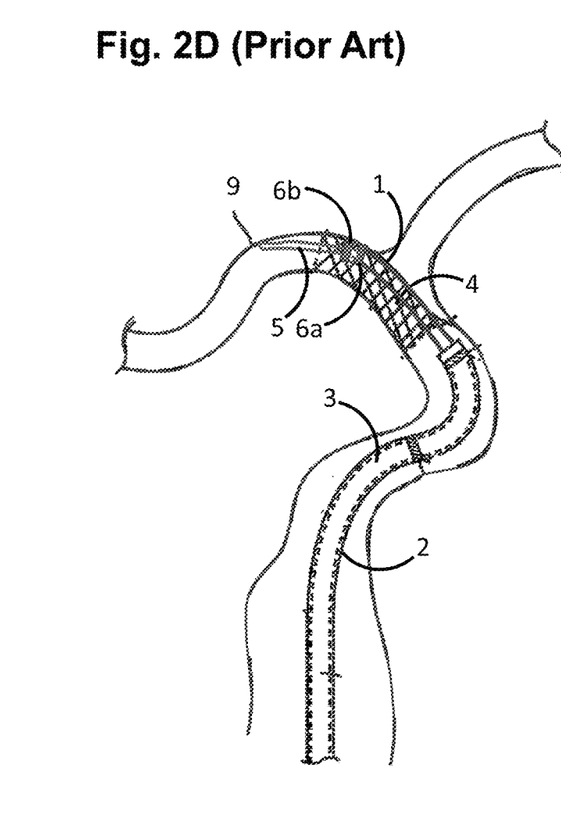

However, crossing the deployed stent 1 with a delivery wire 3 poses challenges due to mechanical interactions between a distal tip 5 and bumpers 6a, 6b of the stent delivery mechanism 3 and the struts of the deployed stent 1. As one example illustrated in FIG. 2C, the distal tip 5 of the delivery wire 4 may dig into the cells of the deployed stent 1, preventing reliable re-crossing of the deployed stent 1, especially when the stent 1 is deployed in a curvature of the vessel 9. Even if the distal tip 3 of the delivery wire 4 is re-crossed over the deployed stent 1, it is desirable to re-cross the deployed stent 1 a sufficient amount, such that the more rigid portion of the delivery wire 3 resides within the deployed stent 1 to facilitate delivery of the balloon catheter into the deployed stent 1. However, the forward edges of the bumper 6a, 6b, which are now exposed due to the removal of the stent 1, may catch on the struts of the stent 1, thereby creating additional challenges for re-crossing the deployed stent 1 a sufficient distance to allow the balloon catheter to be reliably guided into the deployed stent 1, as illustrated in FIG. 2D.

SUMMARY

In exemplary embodiments of the disclosed inventions, an implant delivery system is provided, the system including a delivery catheter having a lumen, an elongate delivery mechanism slidably disposed in the lumen of the delivery catheter, the elongate delivery mechanism comprising an annular channel and a compressible annular bushing disposed within the annular channel, the annular bushing configured for being placed between a compressive profile and an expanded profile, and an implant being coaxially disposed between the delivery catheter and the elongate delivery mechanism, the medical implant comprising a tubular body and at least one engagement element affixed to the tubular body, the lumen of the delivery catheter being sized to maintain the at least one engagement element within the annular channel and to urge the annular bushing into the compressive profile, such that the elongate delivery mechanism and implant can be distally displaced in the lumen of the delivery catheter in unison to deploy the medical implant from the delivery catheter, thereby allowing the annular bushing to assume the expanded profile.

The elongate delivery mechanism may further include a delivery wire having a proximal end and a distal end, a proximal bumper affixed to the distal end of the delivery wire, and a distal bumper affixed to the distal end of the delivery wire distal to the proximal bumper, thereby creating the annular channel between the proximal and distal bumpers. The tubular body of the medical implant may be disposed on the distal end of the delivery wire at a location distal to the distal bumper, in which case the elongate delivery mechanism may include a coil (which may be radiopaque) disposed on the distal end of the delivery wire distal to the distal bumper, and a tubular distal tip affixed over the coil, wherein the tubular body of the medical implant is disposed over the tubular distal tip. The at least one engagement element(s) of the medical implant may be radiopaque, have angled arms, and may be affixed at a proximal edge of the tubular body of the medical implant. The annular bushing of the delivery mechanism may be composed of a polymer such as a polyester-based thermoplastic polyurethane, and when in the expanded profile, the annular bushing may occupy substantially the entire annular space.

An exemplary method of operating the implant delivery system includes inserting the implant delivery system into a blood vessel of a patient adjacent a target site; axially displacing the elongate delivery mechanism within the lumen of the delivery catheter until the medical implant is deployed at the target site, wherein the annular bushing assumes the expanded profile; re-crossing deployed implant with the elongated delivery mechanism until the annular bushing of the elongate delivery mechanism is distal to the deployed implant; removing the delivery catheter from the elongate delivery mechanism; guiding another catheter over the elongate delivery mechanism, while the annular bushing is distal to the deployed implant, until an operative element of the other catheter is adjacent the target site; and operating the operative element to perform a procedure at the target site.

The medical implant may be a stent, the other catheter may be a balloon catheter, and the operative element may be a balloon, wherein the balloon catheter is guided over the elongate delivery mechanism until the balloon is inside of the deployed stent, operating the balloon comprises inflating the balloon, and performing the procedure comprises radially urging the deployed stent against an inner surface of the blood vessel.

The method may further include removing a blockage at the target site within the blood vessel prior to deploying the medical implant at the target site.

The elongate delivery mechanism may be provided with a distal tip that is pre-shaped to assume a curved geometry (e.g., a "j" shape) in the absence of a compressive force, and the tubular body of the medical implant constrains the distal tip of the elongate delivery mechanism to assume a straight geometry, wherein the distal tip of the elongate delivery mechanism may be configured for assuming the curved geometry when the medical implant is deployed out of the delivery catheter. In such embodiments, an exemplary method of operating the implant delivery system includes inserting the implant delivery system into a blood vessel of a patient adjacent a target site; axially displacing the elongate delivery mechanism within the lumen of the delivery catheter until the medical implant is deployed at the target site, wherein the annular bushing assumes the expanded profile and the distal tip of the elongated deliver mechanism assumes curved geometry; re-crossing deployed implant with the elongated delivery mechanism until the distal tip and annular bushing of the elongate delivery mechanism is distal to the deployed implant; removing the delivery catheter from the elongate delivery mechanism; guiding another catheter over the elongate delivery mechanism, while the annular bushing is distal to the deployed implant, until an operative element of the other catheter is adjacent the target site; and operating the operative element to perform a procedure at the target site.

In embodiments in which the tubular body of the medical implant is disposed on the distal end of the delivery wire at a location distal to the distal bumper, an exemplary method of operating the implant delivery system includes inserting the implant delivery system into a blood vessel of the patient adjacent a target site; axially displacing the elongate delivery mechanism within the lumen of the delivery catheter until the medical implant is deployed at the target site, wherein the annular bushing assumes the expanded profile and the distal tip of the elongated deliver mechanism assumes curved geometry; re-crossing deployed implant with the elongated delivery mechanism until the distal tip and annular bushing of the elongate delivery mechanism is distal to the deployed implant; removing the delivery catheter from the elongate delivery mechanism; guiding another catheter over the elongate delivery mechanism, while the annular bushing is distal to the deployed implant, until an operative element of the other catheter is adjacent the target site; and operating the operating element to perform a procedure at the target site.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of exemplary embodiments of the disclosed inventions, in which similar elements are referred to by common reference numerals. It should be noted that the figures are not drawn to scale and that elements of similar structures or functions are represented by like reference numerals throughout the figures. It should also be noted that the figures are only intended to facilitate the detailed description of the embodiments, and are not intended as an exhaustive description thereof or as a limitation on the scope of the disclosed inventions, which is defined only by the appended claims and their equivalents. In addition, various claimed embodiments of the disclosed inventions needs not have all the aspects or advantages depicted in the drawings. An aspect or an advantage described in conjunction with a particular embodiment is not necessarily limited to that embodiment and may be practiced in other embodiments, even if not so illustrated. Understanding that these drawings depict only typical embodiments of the disclosed inventions and are not therefore to be considered limiting of its scope, the disclosed inventions will be described and explained with additional specificity and detail through the use of the accompanying drawings in which:

DETAILED DESCRIPTION OF THE ILLUSTRATED EMBODIMENTS

Figure 3:
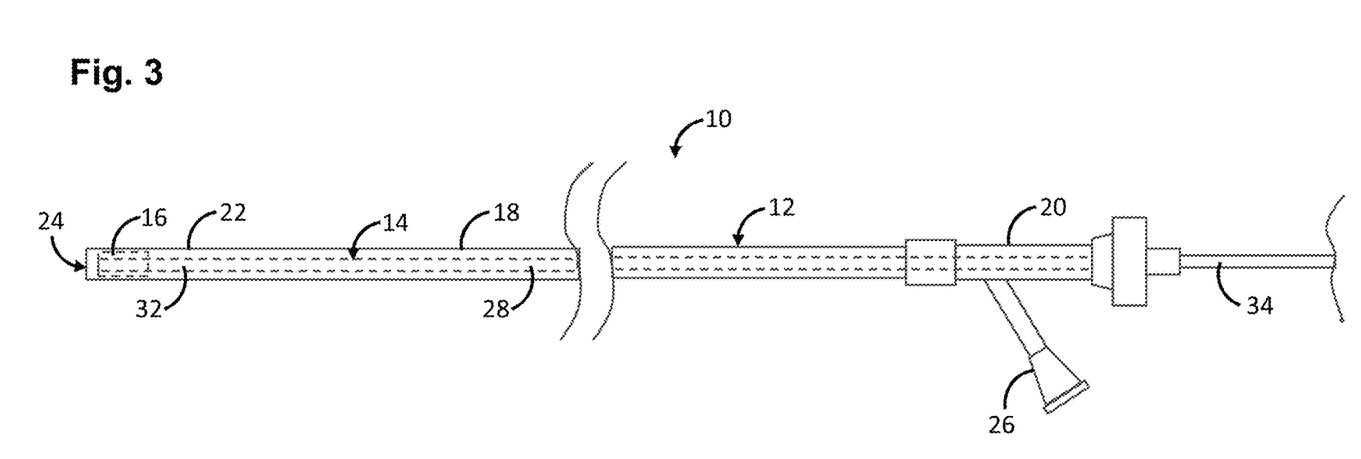
FIG. 3 is a side view of an implant delivery system constructed in accordance with one embodiment of the disclosed inventions.

Referring first to FIG. 3, one embodiment of an implant delivery system 10 constructed in accordance with one embodiment of the disclosed inventions will be described.

The implant delivery system 10 generally comprises an elongate delivery catheter 12, an elongate delivery mechanism 14, and a medical implant 16. In the illustrated embodiment, the stent 16 is described as a stent, although in alternative embodiments, the medical implant can be any tubular implant that allows re-crossing via the elongated delivery mechanism 14, e.g., a flow diverter.

The delivery catheter 12 can, e.g., take the form of a sheath, catheter, micro-catheter or the like. The implant delivery system 10 may be used in an "over-the-wire" configuration, wherein the delivery catheter 12 is introduced into the patient over a guidewire (not shown) that has been previously introduced, and the delivery catheter 12 extends over the entire length of the guidewire (not shown). Alternatively, the implant delivery system 10 may be used in a "rapid-exchange" configuration, where a guidewire (not shown) extends through only a distal portion of the delivery catheter 12 from a guidewire port (not shown). In other alternative embodiments, the implant delivery system 10 may be introduced into the patient after a guidewire had been withdrawn, leaving a sheath or access catheter distal portion at the target site for the implant delivery system 10 to navigate through the vasculature of the patient within the sheath or access catheter.

The delivery catheter 12 may, e.g., comprise a length about 50 cm-300 cm, and typically about 60 cm-200 cm. The delivery catheter 12 is configured for accessing a body lumen, such as a blood vessel, for a desired treatment in a target site. For example, the target site may be within a small diameter blood vessel having a 2-5 mm lumen diameter and accessible by way of a tortuous vessel path, which may involve shar vessel turns and multiple vessel branches. In such cases, the delivery catheter 12 has a small suitable diameter and flexible construction.

In any event, the delivery catheter 12 comprises an elongate sheath body 18 having a proximal portion 20 and a distal portion 22, and an inner lumen 24 extending between the proximal portion 20 and the distal portion 22 of the sheath body 18. The proximal portion 20 of the sheath body 18 remains outside of the patient and accessible to the operator when the implant delivery system 10 is in use, while the distal portion 22 of the sheath body 18 is sized and dimensioned to reach remote locations of a vasculature to deliver the stent 16 to a target location in a patient's body, such as an occlusion in a blood vessel, in a blood vessel adjacent to an aneurysm neck, a bifurcated blood vessel, or the like. The lumen 24 of the delivery catheter 12 is sized to accommodate longitudinal movement of the radially contracted implant 16 and elongate delivery mechanism 14.

The delivery catheter 12 may have at least one fluid port 26 in fluid communication with the lumen 24 to introduce fluids into the delivery catheter 12 in order to hydrate the elongate delivery mechanism 14 and the stent 16. The delivery catheter 12 may include one or more optional marker bands (not shown) formed along the sheath body 18 from a radiopaque material that can be used to identify the location of the distal end of the delivery catheter 12 within the patient's vasculature system, or relative to the undeployed or deployed stent 16, using imaging technology (e.g., fluoroscope imaging).

The delivery catheter 12 may include one or more, or a plurality of regions along its length having different configurations and/or characteristics. For example, the distal portion 22 of the sheath body 18 may have an outer diameter less than the outer diameter of the proximal portion 20 to reduce the profile of the distal portion 22 and facilitate navigation in tortuous vasculature. Furthermore, the distal portion 22 may be more flexible than the proximal portion 20. Generally, the proximal portion 20 may be formed from material that is stiffer than the distal portion 22, so that the proximal portion 20 has sufficient pushability to advance through the patient's vascular system, while the distal portion 22 may be formed of a more flexible material so that the distal portion 22 may remain flexible and track more easily over a guidewire to access remote locations in tortuous regions of the vasculature. In some instances, the proximal portion 20 may include a reinforcement layer, such a braided layer or coiled layer to enhance the pushability of the delivery catheter 12. The delivery catheter 12 may include a transition region between the proximal portion 20 and the distal portion 22.

The sheath body 18 of the delivery catheter 12 may be composed of suitable polymeric materials, metals and/or alloys, such as polyethylene, stainless steel or other suitable biocompatible materials or combinations thereof. Examples of suitable metals and metal alloys can include stainless steel, such as 304V, 304L, and 316L stainless steel; nickel-titanium alloy such as a superelastic (i.e., pseudoelastic) or linear elastic nitinol; nickel-chromium alloy; nickel-chromium-iron alloy; cobalt alloy; tungsten or tungsten alloys; tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or the like; or other suitable metals, or combinations or alloys thereof. Examples of some suitable polymers can include, but are not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polyether-ester, polymer/metal composites, or mixtures, blends or combinations thereof.

The sheath body 18 of the delivery catheter 12 may include a braided-shaft construction of stainless steel flat wire that is encapsulated or surrounded by a polymer coating. By way of non-limiting example, HYDROLENE is a polymer coating that may be used to cover the exterior portion of the sheath body 18. Of course, the system 10 is not limited to a particular construction or type of delivery catheter 12 and other constructions known to those skilled in the art may be used for the sheath body 18 of the delivery catheter 12. The lumen 24 of the delivery catheter 12 may be advantageously coated with a lubricious coating (not shown), such as PTFE, to reduce frictional forces between the sheath body 18 and the elongate delivery mechanism 14 and implant 16 when moved longitudinally within the lumen 24.

The elongate delivery mechanism 14 is slidably disposed in the lumen 24 of the delivery catheter 12, and generally includes a delivery wire 28 having a proximal portion 30 and a distal portion 32. The delivery wire 28 may be composed of a conventional guidewire, torqueable cable tube, or a hypotube. In either case, there are numerous materials that can be used for the delivery wire 28 to achieve the desired properties that are commonly associated with medical devices. Some examples can include metals, metal alloys, polymers, metal-polymer composites, and the like, or any other suitable material.

For example, the delivery wire 28 may include nickel-titanium alloy, stainless steel, a composite of nickel-titanium alloy and stainless steel. In some cases, the delivery wire 28 can be made of the same material along its length, or in some embodiments, can include portions or sections made of different materials. In some embodiments, the material used to construct the delivery wire 28 is selected to impart varying flexibility and stiffness characteristics to different portions of the delivery wire 28. For example, the proximal portion 30 and the distal portion 32 of the delivery wire 28 may be formed of different materials, for example materials having different moduli of elasticity, resulting in a difference in flexibility. For example, the proximal portion 30 can be formed of stainless steel, and the distal portion 32 can be formed of a nickel-titanium alloy. However, any suitable material or combination of material may be used for the delivery wire 28, as desired.

Figure 4:
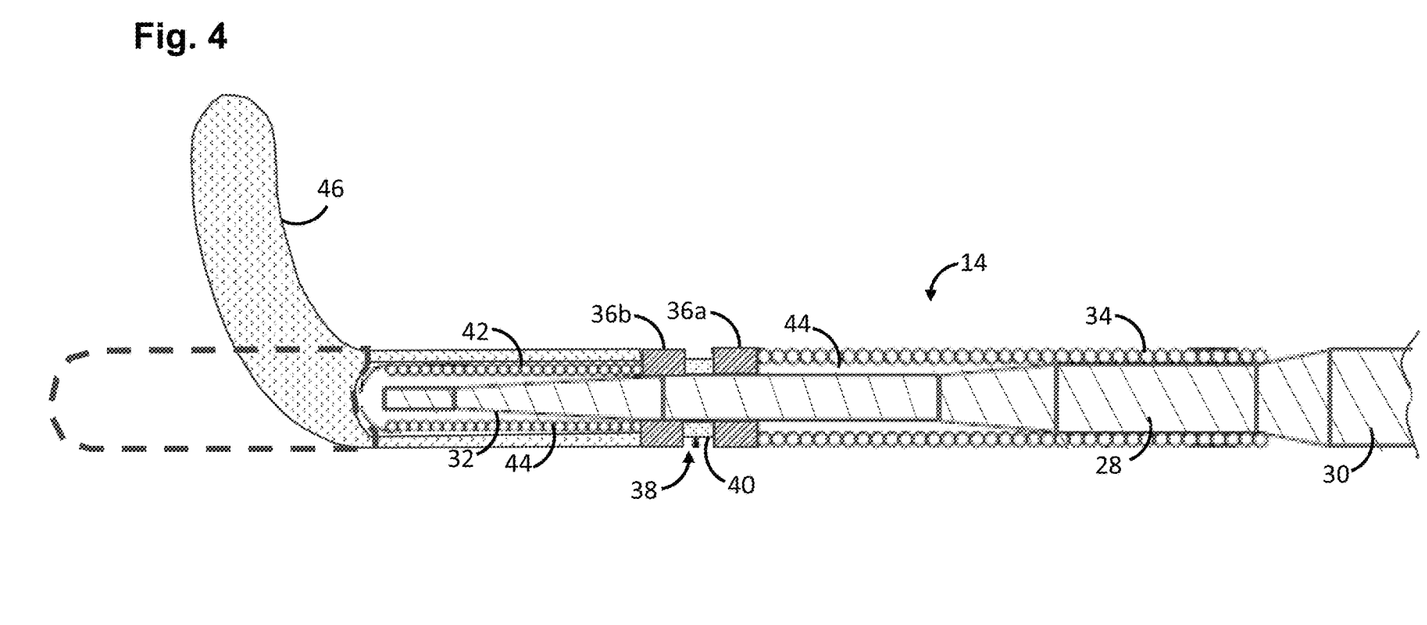
FIG. 4 is a cross-sectional view of one embodiment of an elongate delivery mechanism used in the implant delivery system of FIG. 3.

Referring now to FIG. 4, to increase the flexibility of the distal end of the delivery wire 28, the delivery wire 28 is tapered from a relatively large diameter proximal portion 30 to a relatively small diameter distal portion 32. In this case, the elongate delivery mechanism 14 may further comprise a coil 34 affixed to the transition region of the delivery wire 28 between the proximal portion 30 and the distal portion 32, thereby maintaining lateral flexibility of the elongate delivery mechanism 14 distal to the proximal portion 30, while providing a uniform profile between the proximal portion 30 and the distal portion 32. The elongate delivery mechanism 14 may comprise an optional guidewire lumen (not shown).

The elongate delivery mechanism 14 further comprises a proximal bumper 36a affixed to the distal end 30 of the delivery wire 28, and a distal bumper 36b affixed to the distal end 30 of the delivery wire 28 distal to the proximal bumper 36a, thereby creating an annular channel 38 between the proximal bumper 36a and the distal bumper 36b. The bumpers 36a, 36b may be composed of a suitable biocompatible material, such as stainless steel or nitinol. Each of the bumpers 36a, 36b is disk-shaped, and is sized to engage the lumen 24 of the delivery catheter 12. The outer surfaces of the bumpers 36a, 36b may impart low-fraction due to the material from which they are formed. Alternatively, or additionally, the outer surfaces of the bumpers 36a, 36b may be coated with a lubricious coating, e.g., polytetrafluoroethylene (PTFE), hereby facilitating movement of the bumpers 36a, 36b through the lumen 24 of the delivery catheter 12. Although the bumpers 36a, 36b, and thus, the annular channel 38, preferably have a circular cross-section, the bumpers 36a, 36b and annular channel 38, may have non-circular cross-sections, including irregular shapes. Significantly, the elongate delivery mechanism 14 further comprises an annular bushing 40 disposed within the annular channel 38. The annular bushing 40 is configured for being placed between a compressive profile (FIG. 5A) and an expanded profile (FIG. 5B), as will be discussed in further detail below. The annular bushing 40 may be composed of a suitable material, e.g., a polymeric material, or a non-polymeric material, such as super elastic material, which can be folded in the compressive profile and unfolded in the expanded profile. Preferably, the annular bushing 40 is not rotatably affixed within the annular channel 38, and is therefore free to spin within the annular channel 38.

The elongate delivery mechanism 14 further comprises a coil 42 disposed about the distal end 30 of the delivery wire 28 distal to the distal bumper 36b, preferably in abutment with the distal surface of the distal bumper 36b. The coil 42 may be advantageously radiopaque to aid in visualization of the location and curvature of the distal tip 46 of the elongated delivery mechanism 14 during the re-crossing procedure, as discussed in further detail below. In this case, the coil 42 may be composed of a suitable biocompatible material, such as platinum, gold, tungsten, or alloys thereof or other metals. Alternatively, instead of a coil 42, the elongate delivery mechanism 14 may comprise a material melted down and placed over the distal end 30 of the delivery wire 36 distal to the distal bumper 36b. The elongate delivery mechanism 14 may further comprise a polymer 44 that fills the spaces between the delivery wire 28 and coils 34, 42 to fully integrate the assembly into a unibody design.

Significantly, the elongate delivery mechanism 14 further comprises a distal tip 46 that is pre-shaped to assume a curved geometry (and in the preferred embodiment, J-shaped geometry) when unconstrained, and to assume a straight geometry (shown in phantom) when constrained. In the illustrated embodiment, the distal tip 46 is affixed over the coil 42, although in alternative embodiments, the distal tip 46 may be formed from at least a portion of the delivery wire 28. As will also be discussed in further detail below, the added thickness of the added distal tip 46 increases the diameter of the distal tip of the elongated delivery mechanism 14, as well as creates a bend, that facilitates re-crossing of the deployed stent 16.

As illustrated in FIG. 3, the stent 16 is coaxially disposed between the delivery catheter 12 and the elongate delivery mechanism 14. The elongate delivery mechanism 14 is configured for engaging the stent 16 when the elongate delivery mechanism 14 is axially translated relative to the delivery catheter 12 for delivery of the stent 16 into a target site of a patient. The interface between the elongate delivery mechanism 14 and the stent 16 will be described in further detail below.

Figure 6:
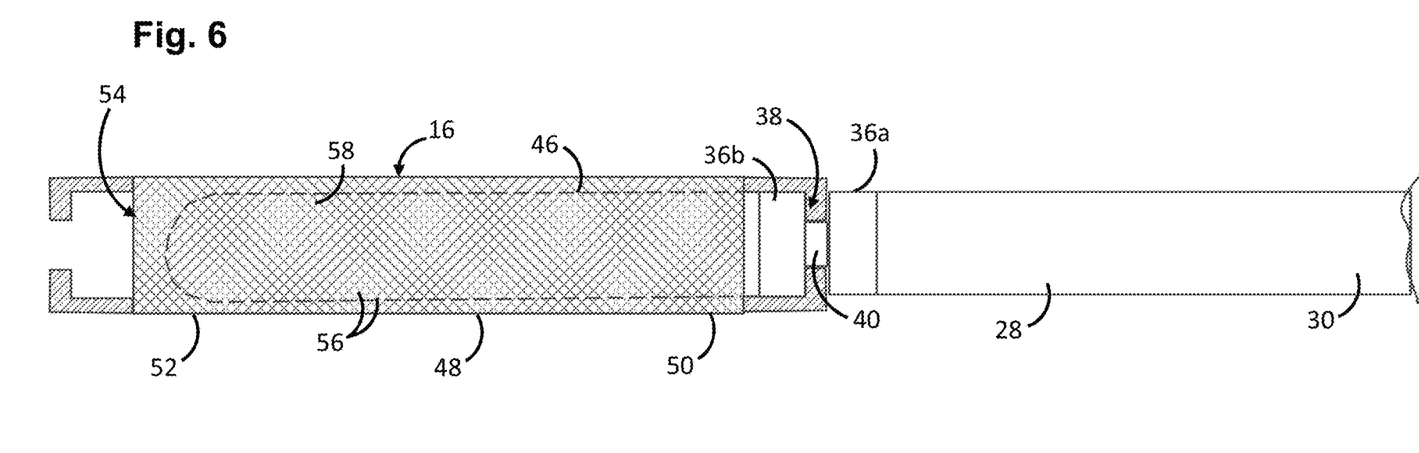
FIG. 6 is a side view of the distal end of the elongate delivery mechanism of FIG. 4, particularly showing an undeployed stent affixed thereto.

Referring to FIG. 6, the stent 16 comprises a tubular resilient body 48 that constrains the distal tip 46 of the elongate delivery mechanism 14 to assume the straight geometry, and releases the constraining force from the distal tip 46 of the delivery mechanism 14 to allow the distal tip 46 of the delivery mechanism 14 to assume the curved geometry once the stent 16 is deployed from the delivery catheter 12. The stent 16 has a proximal portion 50, a distal portion 52, and an inner lumen 54 extending through the tubular body 48 between the proximal portion 50 and the distal portion 52. The stent 16 has a delivery configuration when radially constrained within the lumen 24 of the delivery catheter 12, as illustrated in FIG. 3. Preferably, the cross-sectional dimension of the tubular resilient body 48, when the stent 16 is in the delivery configuration, is the same as cross-sectional dimensions of the bumpers 36a, 36b to facilitate displacement of the elongated delivery mechanism 14 and implant 16 within the delivery catheter 12.

The tubular body 48 of the stent 16 comprises a plurality struts 56 that form cells 58 therebetween, and is biased to expand radially outwards into a deployed configuration when deployed out of the delivery catheter 12. The stent 16 may be constructed of any number of various materials commonly associated with medical devices, including metals, metal alloys, polymers, metal-polymer composites, etc., e.g., stainless steels, cobalt-based alloys, gold alloys, elgioloy, nickel, titanium, platinum, nitinol, shape memory polymers, or combinations thereof. The stent 16 may also be formed in a variety of manners as well. For example, the stent 16 may be formed by etching or cutting a pattern from a tube or sheet of stent material; a sheet of stent material may be cut or etched according to a desired stent pattern whereupon the sheet may be rolled or otherwise formed into the desired substantially tubular, bifurcated or other shape. For the stent 16, one or more wires or ribbons of stent material may be woven, braided or otherwise formed into a desired shape and pattern. The stent 16 may include further components that are welded, bonded or otherwise engaged to one another. The stent 16 may include a non-porous, non-permeable biocompatible material, cover or the like, when the stent 16 is used as a blood flow diverter. Implants 16, such as stents, are further described in U.S. patent application Ser. No. 14/139,815, entitled "Multilayer Stent," filed Dec. 23, 2013, and U.S. patent application Ser. No. 14/104, 906, entitled "Stent Delivery System," filed Dec. 12, 2013, which are expressly incorporated herein by reference.

Figure 7:
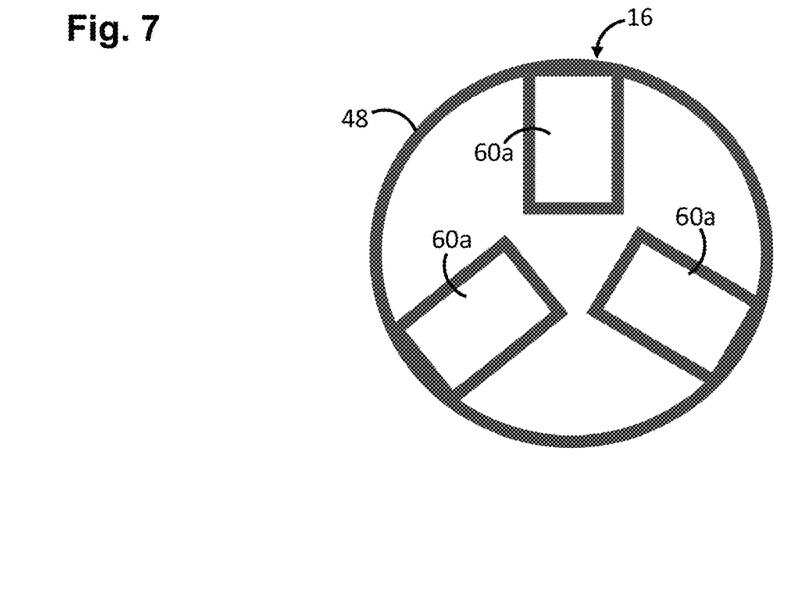
FIG. 7 is an axial view of the stent of FIG. 6, particularly showing the engagement elements of the stent.

Referring further to FIG. 7, the stent 16 further comprises at least one proximal radiopaque marker 60a (in this case, three) formed at a proximal portion 50 of the tubular body 48, and at least one distal radiopaque marker 60b (in this case, three not shown in FIG. 7) formed at a distal portion 52 of the tubular body 48. The radiopaque markers 60a, 60b be composed of a suitable biocompatible material, such as platinum, gold, tungsten, or alloys thereof or other metals. The radiopaque markers 60a, 60b allow the stent 16 to be visualized during its delivery to the target location in the vessel. That is, the proximal marker 60a indicates a location of the proximal end of the stent 16, whereas the distal marker 60b indicates a location of the distal end of the stent 16. Significantly, the proximal radiopaque marker 60a serves as an engagement element that is releasably engaged with the annular channel 38 of the elongate delivery mechanism 14. In the illustrated embodiment, each of the engagement elements 60a takes the form of a resilient angled arm that catches the annular channel 38 of the elongate delivery mechanism 14.

Figure 5A:
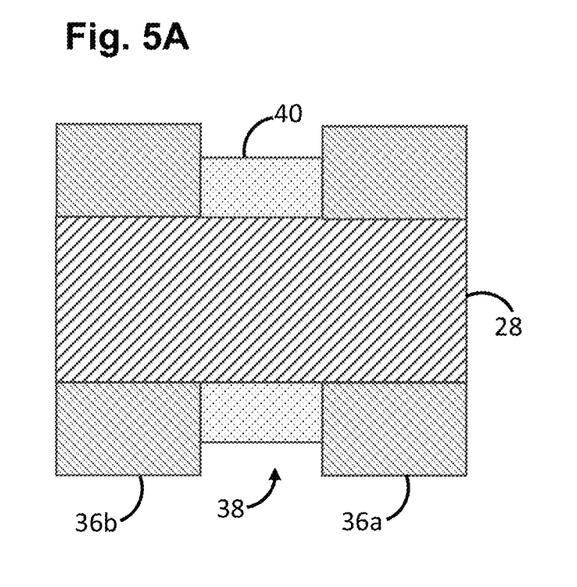
FIG. 5A is a cross-sectional view of one embodiment of a compliant annular bushing used in the elongate delivery mechanism of FIG. 4 to occupy an annular space, particularly showing the annular bushing in a compressed profile.
Figure 5B:
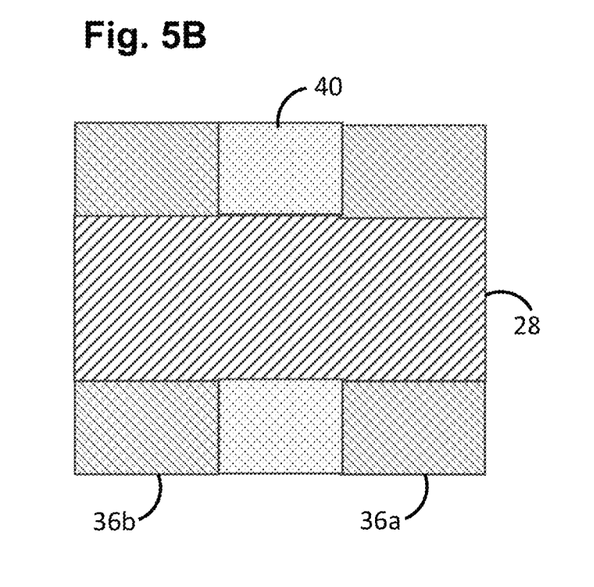
FIG. 5B is a cross-sectional view of the compliant annular of FIG. 5A, particularly shown in an expanded profile.

The resilient angled arms 60a of the stent 16 are biased to be radially displaced in the outward radial direction. However, the lumen 24 of the delivery catheter 12 is sized to maintain the angled arms 60a within the annular channel 38 of the elongated delivery mechanism 14, and to urge the annular bushing 40 into the compressive profile (as shown in FIG. 5a), such that the elongate delivery mechanism 14 and the stent 16 can be distally displaced in the lumen 24 of the delivery catheter 12 in unison to deploy the stent 16 from the delivery catheter 12. Once the stent 16 is deployed from the lumen 24 of the delivery catheter 12, the resilient angled arms 60a will displace in the radial outward direction, thereby disengaging, thereby releasing the stent 16. As will be described in further detail below, the annular bushing 40 will assume the expanded profile (as illustrated in FIG. 5b) after the stent 16 is deployed from the delivery catheter 12, substantially occupying the entirety of the annular channel 38 (i.e., at least 90 percent of the annular channel 38 is occupied), although optimally, the outer surface of the annular bushing 40 is completely flush with the outer surfaces of the bumpers 36a, 36b, thereby completely eliminating any discontinuities in the annular channel 38 that may snag on the deployed stent 16 during a re-crossing process, as will be described in further detail below. Thus, the annular bushing 40 is preferably shaped to occupy the annular channel 38 as much as possible while accommodating the proximal radiopaque marker 60a.

Although the engagement elements 60a have been described as radiopaque angled arms, it should be appreciated that, in alternative embodiments, the engagement elements 60a may not be radiopaque, and may take other forms besides angled arms that are otherwise capable of engaging the annular channel 38 and placing the annular bushing 40 in its compressed profile.

Figure 8:
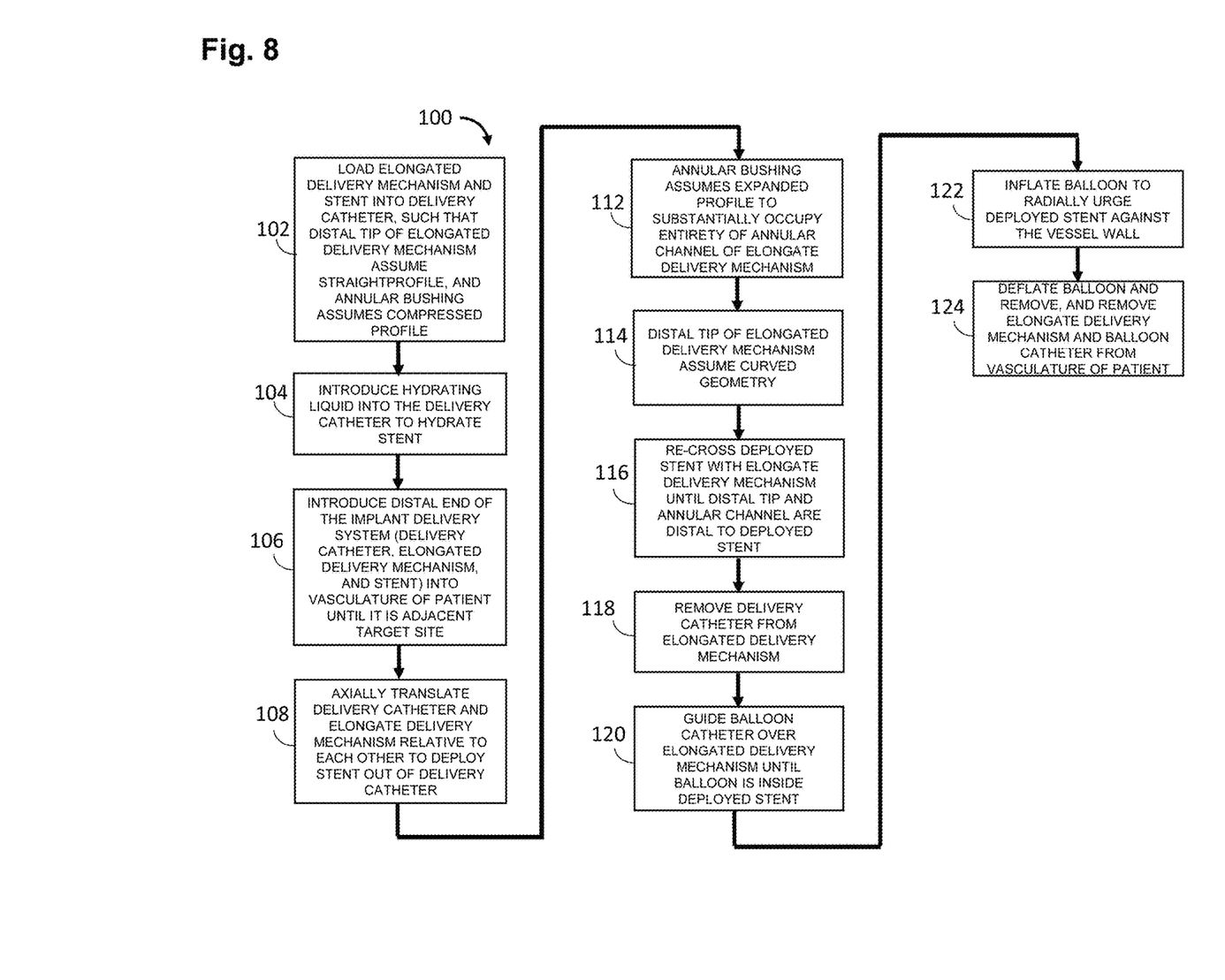
FIG. 8 is a flow diagram illustrating one method of operating the implant delivery system of FIG. 3 to implant a stent within the vasculature of a patient.

Having described the function and structure of the implant delivery system 10, one method 100 of using the implant delivery system 10 illustrated in FIG. 8 will now be described. The method 100 of using the implant delivery system 10 will be described in the context of treating a blockage at a target site of a blood vessel within the vasculature of a patient, and assumes that the blockage has been previously removed from the blood vessel.

First, the elongated delivery mechanism 14 and implant 16 (in this case a stent) is front-loaded into the delivery catheter 12, e.g., by introducing into the proximal end of the delivery catheter 12, and subsequently advancing, the elongated delivery mechanism 14 and implant 16 within the lumen 24 of the delivery catheter 12 until the stent 16 is located at the distal end of the delivery catheter 12 (step 102) (see FIG. 3). This step can be performed by the manufacturer or medical personnel. The stent 16 and bumpers 36a, 36b of the elongated delivery mechanism 14 may be threaded into the proximal end of the delivery catheter 12 using an iris crimper (available from Machine Solutions, Inc.) or a funnel, until the stent 16 is located at the distal end of the delivery catheter 12. At this point, the stent 16 is affixed to the elongate delivery mechanism 14, such that the distal tip 46 of the elongate delivery mechanism 14 is constrained by the stent 16, and therefore, assumes its straight profile (see FIG. 4), and the engagement elements 52 (i.e., the angled arms) of the stent 16 are disposed within the annular channel 38 of the elongate delivery mechanism 14, such that the annular bushing 40 assumes its compressed profile (see FIG. 5A).

Figure 9A:
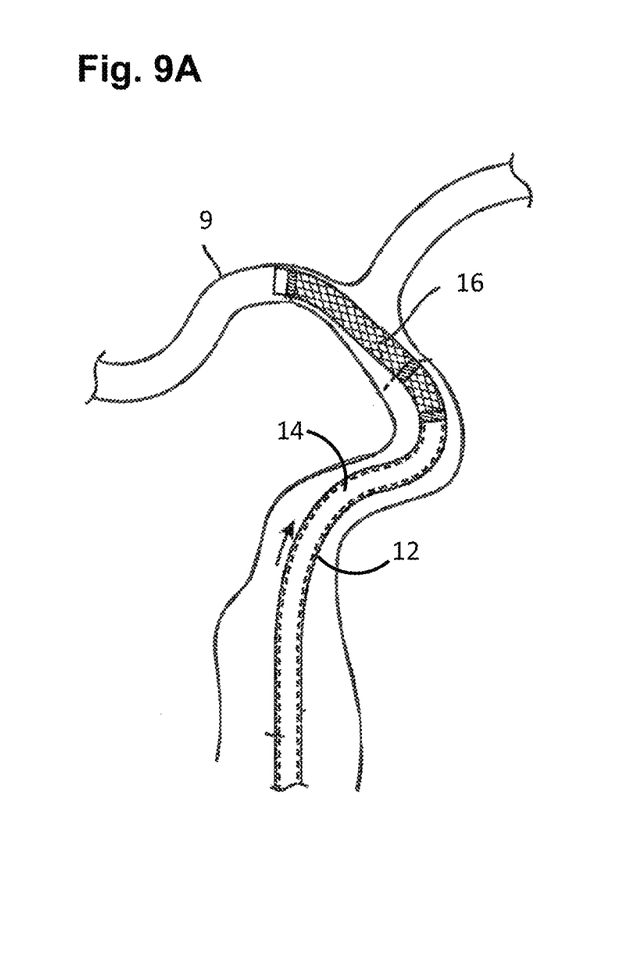
FIGS. 9A-9F are plan views illustrating the method of FIG. 8.

Next, the hydrating liquid, such as normal saline, is introduced into the liquid port at the proximal end 20 of the sheath body 18 of the delivery catheter 12, and travels through the lumen 24 of the sheath body 18 to hydrate the stent 16 (step 104). Next, the distal end of the implant delivery system 10 is introduced into the vasculature of a patient in a conventional manner, and advanced through the vasculature (e.g., over a previously placed guidewire) until the distal portion 20 of the delivery catheter 12 is adjacent a target site within a blood vessel 9 of the patient (step 106) (see FIG. 9A). The radiopaque markers (not shown) on the distal portion 20 of the sheath body 18 may aid in visualizing the delivery catheter relevant to anatomical landmarks as the delivery catheter 12 is guided through the vasculature. The implant delivery system 10 may be introduced into the vasculature of the patient in unison, in which case, the elongated delivery mechanism 14 and stent 16 may first be loaded into the delivery catheter 12, as discussed above with respect to step 102, or delivery catheter 12, without the elongated delivery mechanism 14 and stent 16, can first be introduced into the vasculature of the patient and advanced to the target site of the blood vessel, and then the elongated delivery mechanism 14 and stent 16 can then be loaded into the delivery catheter 12 in the manner described above with respect to step 102.

Figure 9B:
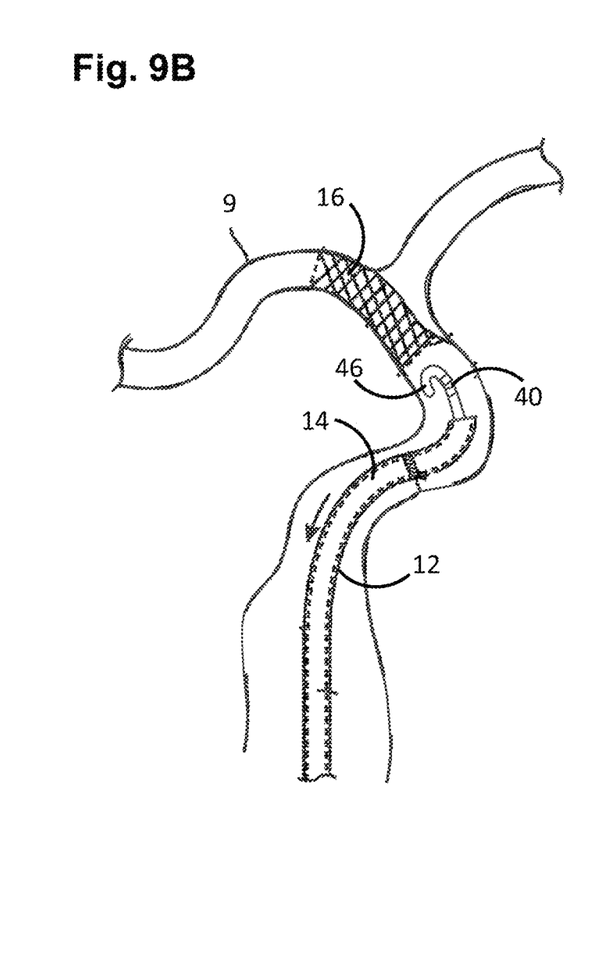

Next, the delivery catheter 12 and elongate delivery mechanism 14 are axially translated relative to each other (e.g., by pulling the delivery catheter 12 in the proximal direction, by pushing the elongate delivery mechanism 14 in the distal direction, or both), thereby distally advancing implant 16 (in this case, a stent) within the lumen 24 of the delivery catheter 12 until the stent 16 deploys out of the lumen 24 of the delivery catheter 12 at the target site of the blood vessel 9 (step 108) (see FIG. 9B). As a result of the deployment of the stent 16, and thus, the release of the compressive force by the delivery catheter 12 on the distal end of the elongate delivery mechanism 14, the resiliency of the engagement elements 60a (i.e., the angled arms) of the stent 16 cause them to radially move outward from the annular channel 38 between the bumpers 36a, 36b, releasing the stent 16 from the elongate delivery mechanism 14, which allows the annular bushing 40 of the elongate delivery mechanism 14 to assume the expanded profile (step 110), and the distal tip 46 of the elongate delivery mechanism 14 to assume its curved geometry (in this case, a J-shape) (step 112) (see FIG. 9B). Thus, the expanded annular bushing 40 substantially occupies the entirety of the annular channel 38 (see FIG. 5B), and the distal tip 46 curves back on itself, thereby eliminating any edges and low-profile mechanisms that may hinder re-crossing of deployed stent 16 by the elongate delivery mechanism 14. The radiopaque markers of the stent 18 (in this case, the proximal and distal markers 60a, 60b) allow visualization of the stent 18 relative to the delivery catheter 12 and other anatomical features adjacent the target site.

Figure 9C:
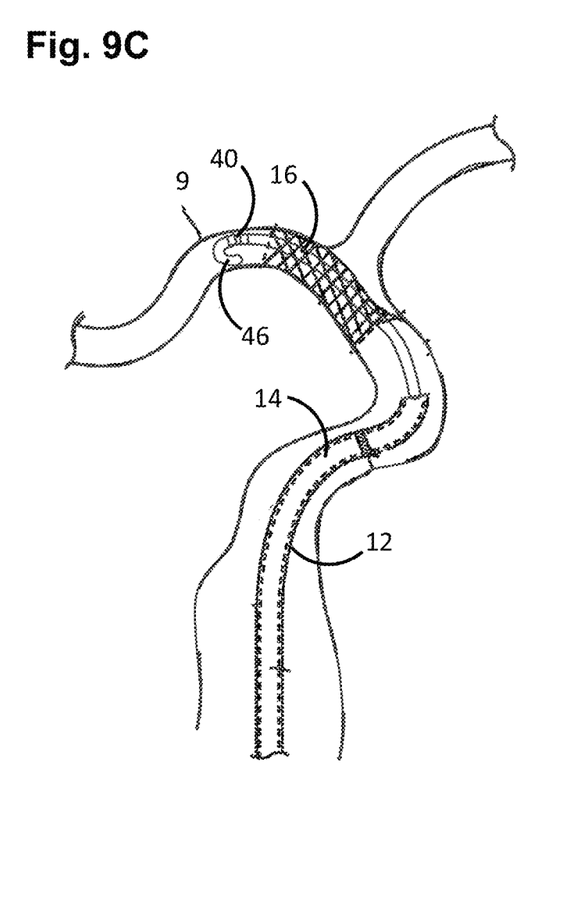
Figure 9D:
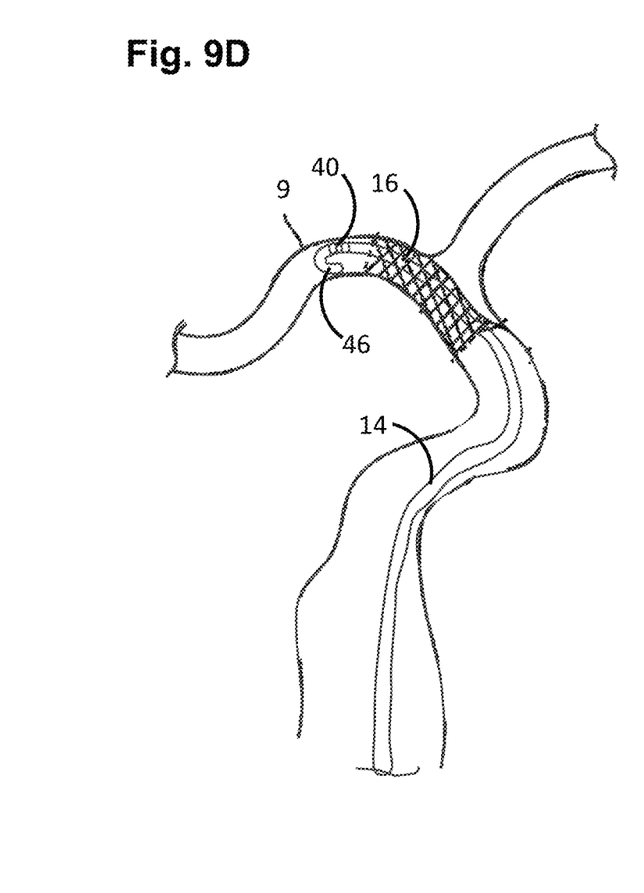
Figure 9E:
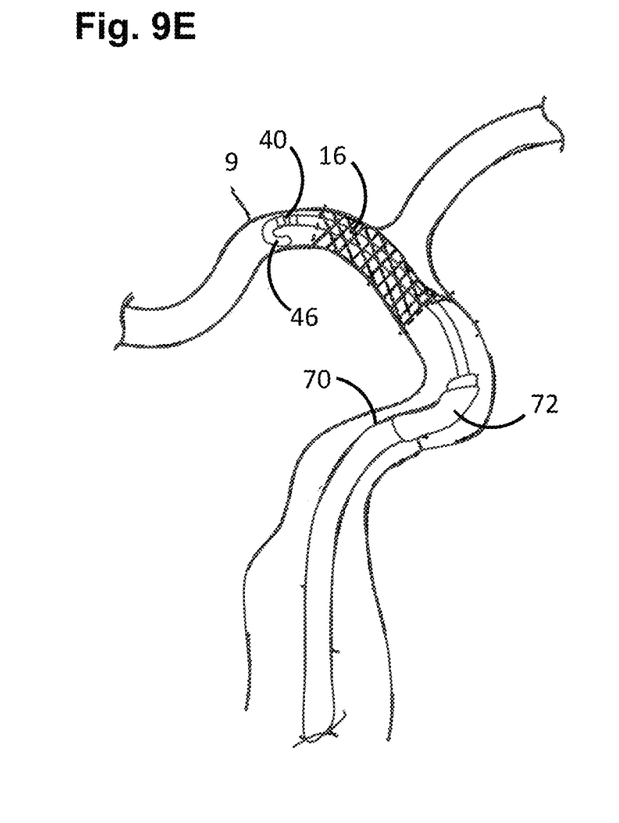
Figure 9F:
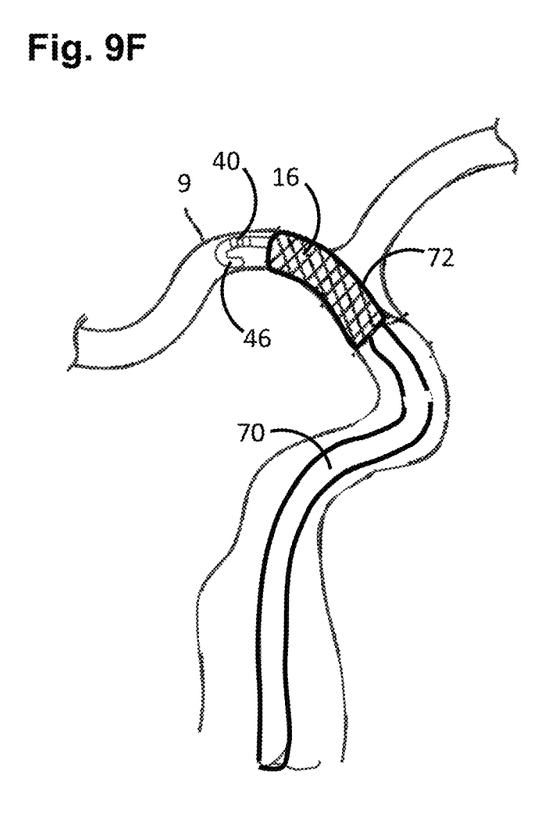

Next, the deployed stent 16 is re-crossed with the distal end of the elongate delivery mechanism 14 until distal tip 46 and annular channel 38 are distal to the deployed stent 16 (step 116) (see FIG. 9C). The combination of the increased diameter and J-shape of the distal tip 46 of the elongated delivery mechanism 14, as well as the expansion of the annular bushing 40 within the annular channel 38 between the bumpers 36a, 36b of the elongated delivery mechanism 14, avoids or at least minimizes the possibility that the elongated delivery mechanism 14 will catch or snag on the struts of the stent 16 during the re-crossing procedure. The radiopaque marker at the distal end of the elongate delivery mechanism 14 (in this case, the coil 42 disposed at the distal portion 32 of the delivery wire 28), allows visualization of the location and shape of the distal tip 46 relative to the stent 16 during the stent re-crossing procedure. The delivery catheter 12 is removed from the elongate delivery mechanism 14 (see FIG. 9D), ultimately being entirely removed from the patient (step 118). The delivery catheter 12 may be removed prior to or subsequent to the stent re-crossing procedure. Another catheter 70 (in this case, a balloon catheter) is guided over the elongate delivery mechanism 14, while the distal tip 46 and annular channel 38 are distal to the deployed stent 16, until an operative element 72 (in this case, a balloon) of the balloon catheter 70 is adjacent to the target site (in this case, inside of the deployed stent 16) (step 120) (see FIG. 9E). The balloon catheter 70 is then operated, and in particular, the balloon 72 is inflated to radially urge the deployed stent 16 against the wall of the vessel in order to support and reinforce the wall of the vessel, while maintaining the vessel in an open, unobstructed condition (step 122) (see FIG. 9F). The balloon 72 is then deflated, and the elongate delivery mechanism 14 and balloon catheter 70 are removed from the patient (step 124).

Although particular embodiments of the disclosed inventions have been shown and described, it should be understood that the present inventions are not limited to the illustrated embodiments, and that various changes and modifications may be made thereto without departing from the scope of the present inventions, which is limited only by the following claims and their equivalents.

What is claimed is:

1. An implant delivery system, comprising:
   a delivery catheter having a lumen;
   an elongate delivery mechanism slidably disposed in the lumen of the delivery catheter, the elongate delivery mechanism comprising
      a delivery wire having a proximal end and a distal end,
      a proximal bumper affixed to the distal end of the delivery wire,
      a distal bumper affixed to the distal end of the delivery wire distal to the proximal bumper, thereby creating an annular channel between the proximal and distal bumpers, and
      a compressible annular bushing disposed within the annular channel, the annular bushing configured for being placed between a compressive profile and an expanded profile; and
   a medical implant being coaxially disposed between the delivery catheter and the elongate delivery mechanism, the medical implant comprising a tubular body and at least one engagement element affixed to the tubular body, the lumen of the delivery catheter being sized to maintain the at least one engagement element within the annular channel and to urge the annular bushing into the compressive profile, such that the elongate delivery mechanism and implant can be distally displaced in the lumen of the delivery catheter in unison to deploy the medical implant from the delivery catheter, thereby allowing the annular bushing to assume the expanded profile,
   wherein the tubular body of the medical implant is disposed on the distal end of the delivery wire at a location distal to the distal bumper.

2. The implant delivery system of claim 1, wherein the elongate delivery mechanism further comprises:
   a coil disposed on the distal end of the delivery wire distal to the distal bumper; and
   a tubular distal tip affixed over the coil, wherein the tubular body of the medical implant is disposed over the tubular distal tip.

3. The implant delivery system of claim 2, wherein the coil is radiopaque.

4. A method of operating the implant delivery system of claim 2 in a patient, comprising:
   inserting the implant delivery system into a blood vessel of the patient adjacent a target site;
   axially displacing the elongate delivery mechanism within the lumen of the delivery catheter until the medical implant is deployed at the target site, wherein the annular bushing assumes the expanded profile and the distal tip of the elongate delivery mechanism assumes a curved geometry;
   re-crossing the deployed implant with the elongate delivery mechanism until the distal tip and annular bushing of the elongate delivery mechanism is distal to the deployed implant;
   removing the delivery catheter from the elongate delivery mechanism;
   guiding another catheter over the elongate delivery mechanism, while the annular bushing is distal to the deployed implant, until an operative element of the other catheter is adjacent the target site; and
   operating the operating element to perform a procedure at the target site.

5. The method of claim 4, wherein the medical implant is a stent, the other catheter is a balloon catheter, and the operative element is a balloon, wherein the balloon catheter is guided over the elongate delivery mechanism until the balloon is inside of the deployed stent, wherein operating the balloon comprises inflating the balloon, and wherein performing the procedure comprises radially urging the deployed stent against an inner surface of the blood vessel.

6. The method of claim 4, further comprising removing a blockage at the target site of the blood vessel prior to deploying the medical implant at the target site.

7. The implant delivery system of claim 1, wherein at least one of the at least one engagement element comprises an angled arm.

8. The implant delivery system of claim 1, wherein the at least one engagement element is affixed at a proximal edge of the tubular body of the medical implant.

9. The implant delivery system of claim 1, wherein at least one of the at least one engagement element is radiopaque.

10. The implant delivery system of claim 1, wherein the annular bushing, when in the expanded profile, occupies substantially the entire annular space.

11. The implant delivery system of claim 1, wherein the annular bushing of the delivery mechanism is composed of a polyester-based thermoplastic polyurethane.

12. The implant delivery system of claim 1, wherein the elongate delivery mechanism has a distal tip that is pre-shaped to assume a curved geometry in the absence of a compressive force, and the tubular body of the medical implant constrains the distal tip of the elongate delivery mechanism to assume a straight geometry, wherein the distal tip of the elongate delivery mechanism is configured for assuming the curved geometry when the medical implant is deployed out of the delivery catheter.

13. A method of operating the implant delivery system of claim 12 in a patient, comprising:
   inserting the implant delivery system into a blood vessel of the patient adjacent a target site;
   axially displacing the elongate delivery mechanism within the lumen of the delivery catheter until the medical implant is deployed at the target site, wherein the annular bushing assumes the expanded profile and the distal tip of the elongate delivery mechanism assumes the curved geometry;
   re-crossing the deployed implant with the elongate delivery mechanism until the distal tip and annular bushing of the elongate delivery mechanism is distal to the deployed implant;
   removing the delivery catheter from the elongate delivery mechanism;
   guiding another catheter over the elongate delivery mechanism, while the annular bushing is distal to the deployed implant, until an operative element of the other catheter is adjacent the target site; and
   operating the operative element to perform a procedure at the target site.

14. The method of claim 13, wherein the medical implant is a stent, the other catheter is a balloon catheter, and the operative element is a balloon, wherein the balloon catheter is guided over the elongate delivery mechanism until the balloon is inside of the deployed stent, wherein operating the balloon comprises inflating the balloon, and wherein performing the procedure comprises radially urging the deployed stent against an inner surface of the blood vessel.

15. The method of claim 13, further comprising removing a blockage at the target site of the blood vessel prior to deploying the medical implant at the target site.

16. A method of operating the implant delivery system of claim 1 in a patient, comprising:
   inserting the implant delivery system into a blood vessel of the patient adjacent a target site;
   axially displacing the elongate delivery mechanism within the lumen of the delivery catheter until the medical implant is deployed at the target site, wherein the annular bushing assumes the expanded profile;
   re-crossing the deployed implant with the elongated delivery mechanism until the annular bushing of the elongate delivery mechanism is distal to the deployed implant;
   removing the delivery catheter from the elongate delivery mechanism;
   guiding another catheter over the elongate delivery mechanism, while the annular bushing is distal to the deployed implant, until an operative element of the other catheter is adjacent the target site; and
   operating the operative element to perform a procedure at the target site.

17. The method of claim 16, wherein the medical implant is a stent, the other catheter is a balloon catheter, and the operative element is a balloon, wherein the balloon catheter is guided over the elongate delivery mechanism until the balloon is inside of the deployed stent, wherein operating the balloon comprises inflating the balloon, and wherein performing the procedure comprises radially urging the deployed stent against an inner surface of the blood vessel.

18. The method of claim 16, further comprising removing a blockage at the target site within the blood vessel prior to deploying the medical implant at the target site.

* * * * *